United States Patent
Konishi et al.

(12)

(10) Patent No.: US 6,300,534 B1
(45) Date of Patent: Oct. 9, 2001

(54) PROCESS FOR PRODUCING DEHYDROGENATED COMPOUNDS OF M-ETHYLDIPHENYLALKANE

(75) Inventors: Tomohiro Konishi, Kanagawa; Kazuharu Suyama, Tokyo, both of (JP)

(73) Assignee: Nippon Petrochemicals Company, Limited, Tokyo (JP)

( * ) Notice: Subject to any disclaimer, the term of this patent is extended or adjusted under 35 U.S.C. 154(b) by 0 days.

(21) Appl. No.: 09/486,369

(22) PCT Filed: Jun. 30, 1999

(86) PCT No.: PCT/JP99/03511

§ 371 Date: Feb. 28, 2000

§ 102(e) Date: Feb. 28, 2000

(87) PCT Pub. No.: WO00/01644

PCT Pub. Date: Jan. 13, 2000

(30) Foreign Application Priority Data

Jul. 1, 1998 (JP) .................................. 10-186295

(51) Int. Cl.⁷ ............................ C07C 5/367; C07C 5/373
(52) U.S. Cl. ...................... 585/441; 585/436; 585/443; 585/444; 585/445
(58) Field of Search ............................... 585/25, 26, 323, 585/320, 436, 441, 443, 444, 445, 459, 463, 462; 560/101; 562/491; 568/429

(56) References Cited

U.S. PATENT DOCUMENTS

| Re. 29,857 | 12/1978 | Argauer et al. | 208/111.05 |
|---|---|---|---|
| Re. 32,162 | 5/1986 | Sato et al. | 346/213 |
| 1,908,190 | 5/1933 | Scholkopf | 568/628 |
| 2,282,327 | 5/1942 | Dreisbach | 585/476 |
| 2,981,765 | 4/1961 | Fetterly | 585/426 |
| 3,043,886 | 7/1962 | Serres, Jr. et al. | 570/199 |
| 3,248,339 | 4/1966 | Spes et al. | 502/1 |
| 3,702,886 | 11/1972 | Argauer et al. | 423/705 |
| 3,709,979 | 1/1973 | Chu | 423/700 |
| 3,758,403 | 9/1973 | Rosinski et al. | 502/67 |
| 3,786,107 | 1/1974 | Kuribayashi et al. | 208/141 |
| 3,790,471 | 2/1974 | Argauer et al. | 208/111.15 |
| 3,832,449 | 8/1974 | Rosinski et al. | 423/205 |
| 3,836,383 | 9/1974 | Kiritani et al. | 503/213 |
| 3,926,782 | 12/1975 | Plank et al. | 208/135 |
| 3,936,566 | 2/1976 | Sato et al. | 503/213 |

(List continued on next page.)

FOREIGN PATENT DOCUMENTS

| 3127905 | 2/1983 | (DE) . |
|---|---|---|
| 1475973 | 6/1977 | (GB) . |
| 1555728 | 11/1979 | (GB) . |
| 46-10064 | 3/1971 | (JP) . |
| 62-41656 | 9/1983 | (JP) . |
| 1013048 | 1/1989 | (JP) . |
| 1013052 | 1/1989 | (JP) . |
| 1-180835 | 7/1989 | (JP) . |
| 2101041 | 4/1990 | (JP) . |
| 02134332 A | 5/1990 | (JP) . |
| 3031221 | 2/1991 | (JP) . |
| WO 88/07032 | 9/1998 | (JP) . |

OTHER PUBLICATIONS

Yamada et al., "Catalytic Decomposition of 1,1–diphenylethane," J. Chem. Soc. Jpn., Ind. Chem. Sect., 72,[7] (1969) pp. 1512–1515 (abstract only).

Walker, J., "Formaldehyde," ACS Monograph Series, Reinhold Publishing Corp., New York, pp. 436–437 (year not available).

Climent et al., "Condensation of Formaldehyde with Benzene in the Presence of HY Zeolites," Applied Catalysis, 51 (1989) pp. 113–125.

*Primary Examiner*—Walter D. Griffin
*Assistant Examiner*—Thuan D. Dang
(74) *Attorney, Agent, or Firm*—Hollander Law Firm, P.L.C.

(57) ABSTRACT

A mono-olefin hydrocarbon and/or a di-olefin hydrocarbon represented by the following general formula (3) is selectively produced by dehydrogenating or oxidative-dehydrogenating a mixture of any one of hydrocarbons among the hydrocarbons represented by the following general formula (1) and any one of hydrocarbons among the hydrocarbons represented by the following general formula (2), followed by distillation;

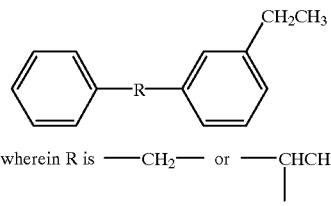

(1)

(wherein R is —CH$_2$— or —CHCH$_3$)

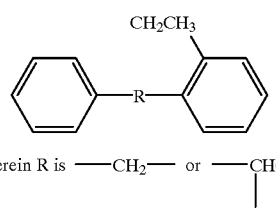

(2)

(wherein R is —CH$_2$— or —CHCH$_3$)

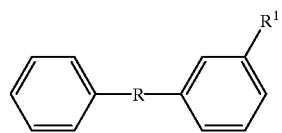

(3)

(wherein R is —CH$_2$— or —CHCH$_3$ or —C=CH$_2$, and R$^1$ is a vinyl or an ethyl group).

7 Claims, No Drawings

U.S. PATENT DOCUMENTS

| | | | |
|---|---|---|---|
| 3,965,209 | 6/1976 | Butter et al. | 585/454 |
| 4,011,278 | 3/1977 | Plank et al. | 585/422 |
| 4,035,285 | 7/1977 | Owen et al. | 208/120.01 |
| 4,111,825 | 9/1978 | Schulz et al. | 585/24 |
| 4,117,026 | 9/1978 | Haag et al. | 585/475 |
| 4,219,687 | 8/1980 | Dolhyj et al. | 585/267 |
| 4,228,024 | 10/1980 | Schulz et al. | 585/6.3 |
| 4,289,806 | 9/1981 | Sato et al. | 417/150 |
| 4,306,106 | 12/1981 | Kerr et al. | 585/640 |
| 4,365,103 | 12/1982 | Chang et al. | 585/320 |
| 4,454,364 | 6/1984 | Farcasiu et al. | 585/470 |
| 4,463,209 | 7/1984 | Kursewicz et al. | 585/467 |
| 4,476,330 | 10/1984 | Kerr et al. | 585/640 |
| 4,523,044 | 6/1985 | Commandeur et al. | 585/11 |
| 4,642,730 | 2/1987 | Sato et al. | 361/315 |
| 4,681,980 | 7/1987 | Sato et al. | 585/6.3 |
| 4,686,548 | 8/1987 | Takahashi et al. | 503/213 |
| 4,870,221 | 9/1989 | Sato et al. | 585/6.3 |
| 4,895,988 | 1/1990 | Clerici et al. | 568/727 |
| 4,899,009 | 2/1990 | Kawakami et al. | 585/471 |
| 4,902,841 | 2/1990 | Kawakami et al. | 585/6.3 |
| 4,922,052 | 5/1990 | Shimizu et al. | 585/25 |
| 4,982,007 * | 1/1991 | Shimizu et al. | 568/429 |
| 4,982,025 | 1/1991 | Kawakami et al. | 585/6.3 |
| 4,999,450 * | 3/1991 | Shimizu et al. | 560/101 |
| 5,068,481 | 11/1991 | Akatsi et al. | 585/426 |
| 5,073,655 | 12/1991 | Angevine et al. | 585/467 |
| 5,171,906 | 12/1992 | Kawakami et al. | 585/25 |
| 5,877,362 | 3/1999 | Dohi et al. | 585/25 |
| 5,880,322 | 3/1999 | Dohi et al. | 585/464 |

* cited by examiner

PROCESS FOR PRODUCING DEHYDROGENATED COMPOUNDS OF M-ETHYLDIPHENYLALKANE

FIELD OF THE INVENTION

The present invention relates to a process for producing hydrocarbons, and more specifically, relates to a process for selectively producing (m-vinylphenyl)phenylmethane, 1-(m-vinylphenyl)-1-phenylethane, 1-(m-ethylphenyl)-1-phenylethylene, or 1-(m-vinylphenyl)-1-phenylethylene which is a useful compound as a synthetic raw material of α-(m-benzoylphenyl)propionic acid (tradename: Ketoprofen) of a profen analgesic.

BACKGROUND ART

A mixture comprising an o-ethyldiphenylalkane and a m-ethyldiphenylalkane can be industrially produced in low cost utilizing an alkylation reaction, a disproportionation reaction, a condensation reaction and the like in the presence of an acid catalyst from a raw material such as an alkylbenzene.

Hereby, α-(m-benzoylphenyl)propionic acid (tradename: Ketoprofen) of a profen analgesic is obtained by a reaction such as a carbonylation from 1-(m-vinylphenyl)-1-phenylethane in Japanese Patent Application Laid-open No. Hei 2-101041. In addition, α-(m-benzoylphenyl)propionic acid of a profen analgesic is obtained from 1-(m-vinylphenyl)-1-phenylethylene in Japanese Patent Application Laid-open No. Hei 3-31221. Further, in U.S. Pat. No. 4,922,052 (m-vinylphenyl)phenylmethane or the like is produced using a Grignard reagent, and α-(m-benzoylphenyl)propionic acid (tradename: Ketoprofen) of a profen analgesic is obtained therefrom.

Any of the processes for producing α-(m-benzoylphenyl)propionic acid (tradename: Ketoprofen) of a profen analgesic from the above-mentioned 1-(m-vinylphenyl)-1-phenylethane, 1-(m-vinylphenyl)-1-phenylethylene, (m-vinylphenyl)phenylmethane is according to a cheap and simple process such as carbonylation or the like. Accordingly, it should be said that 1-(m-vinylphenyl)-1-phenylethane, 1-(m-vinylphenyl)-1-phenylethylene, (m-vinylphenyl)phenylmethane and the like are useful as a raw material for α-(m-benzoylphenyl)propionic acid (tradename: Ketoprofen) of a profen analgesic.

Hereby, as already described, the mixture comprising the o-ethyldiphenylalkane and the m-ethyldiphenylalkane can be industrially produced in low cost utilizing an alkylation reaction, a disproportionation reaction, a condensation reaction and the like in the presence of an acid catalyst from an alkylbenzene and the like.

Therefore, if 1-(m-vinylphenyl)-1-phenylethane, 1-(m-vinylphenyl)-1-phenylethylene, (m-vinylphenyl)phenylmethane and the like can be obtained utilizing the mixture, it is industrially advantageous.

However, anethyldiphenylalkane is obtained as a mixture comprising an o-ethyldiphenylalkane, a m-ethyldiphenylalkane and a p-ethyldiphenylalkane by the process utilizing an alkylation reaction, a disproportionation reaction, a condensation reaction and the like in the presence of an acid catalyst from a raw material such as an alkylbenzene or the like.

The boiling points of o-, m- and p-(ethylphenyl)phenylmethane are 290.9° C., 291.5° C. and 297.0° C. respectively. In addition, the boiling points of o-, m- and p-1-(ethylphenyl)-1-phenylethane are 285° C., 284° C. and 293° C.

Accordingly, in case of a p-ethyldiphenylalkane, the p-ethyldiphenylalkane can be separated by a usual separation method of distillation from a mixture of ethyldiphenylalkanes containing thereof.

However, it is practically difficult to separate a m-ethyldiphenylalkane from a mixture comprising an o-ethyldiphenylalkane and a m-ethyldiphenylalkane by distillation. Therefore, it is considered the process of using the mixture comprising the above-mentioned o-ethyldiphenylalkane, m-ethyldiphenylalkane and p-ethyldiphenylalkane as a raw material is difficult to be industrially adopted. In fact, such proposal is not proposed yet.

DISCLOSURE OF THE INVENTION

An object of the present invention is to provide a process for selectively producing (m-vinylphenyl)phenylmethane, 1-(m-vinylphenyl)-1-phenylethane, 1-(m-ethylphenyl)-1-phenylethylene, or 1-(m-vinylphenyl)-1-phenylethylene which is a useful compound as a synthetic raw material of α-(m-benzoylphenyl)propionic acid (tradename: Ketoprofen) of a profen analgesic, utilizing a mixture of an o-ethyldiphenylalkane and a m-ethyldiphenylalkane which are difficult to be separated by an industrial distillation and whose ingredients are difficult to be utilized, as a raw material.

Namely, the present invention is a process for producing hydrocarbons, wherein a mono-olefin hydrocarbon and/or a di-olefin hydrocarbon represented by the following general formula (3) is selectively produced by dehydrogenating or oxidative-dehydrogenating a mixture of any one of hydrocarbons among the hydrocarbons represented by the following general formula (1) and any one of hydrocarbons among the hydrocarbons represented by the following general formula (2), to be distilled.

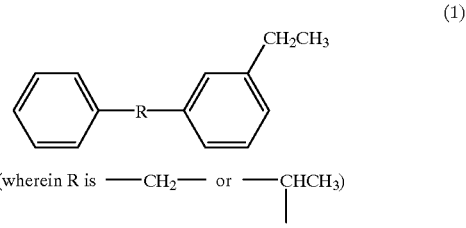

(wherein R is —CH$_2$— or —CHCH$_3$)   (1)

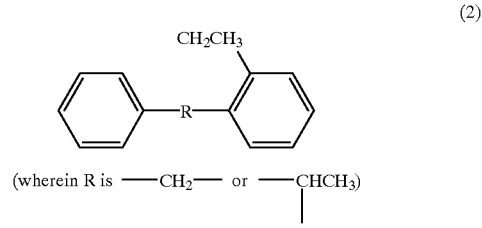

(wherein R is —CH$_2$— or —CHCH$_3$)   (2)

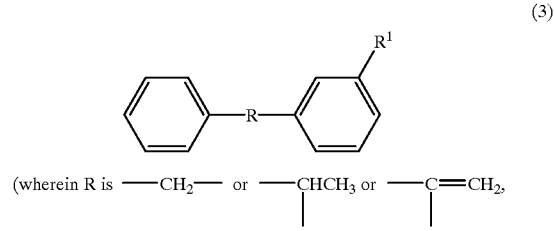

(wherein R is —CH$_2$— or —CHCH$_3$ or —C=CH$_2$,   (3)

and R$^1$ is a vinyl group or an ethyl group)

According to the process for producing hydrocarbons of the present invention, a mixture of an o-ethyldiphenylalkane and a m-ethyldiphenylalkane which are difficult to be separated by an industrial distillation and whose ingredients are difficult to be utilized as a mixture in the prior art can be used as a raw material. When a dehydrogenation reaction is carried out using the raw material, the o-ethyldiphenylalkane in the mixture is a cyclo-dehydrogenated compound having a higher boiling point than the dehydrogenating compound of the m-ethyldiphenylalkane, a solid cyclo-dehydrogenated compound, and a compound obtained by eliminating an ethyl group which was substituted at a phenyl group, i.e., a compound having a lower boiling point than the dehydrogenated compound of the m-ethyldiphenylalkane. Accordingly, the dehydrogenated compound of the o-ethyldiphenylalkane can be easily separated from the dehydrogenated compound of the m-ethyldiphenylalkane by usually distilling a mixture of the dehydrogenation reaction after reaction. As a result, the dehydrogenated compound of the m-ethyldiphenylalkane which is the objective product of the present invention can be easily obtained in high purity.

BEST MODE FOR CARRYING OUT THE INVENTION

The content of the present invention is illustrated in more detail below.

The hydrocarbon represented by the aforementioned general formula (1) is specifically (m-ethylphenyl)phenylmethane or 1-(m-ethylphenyl)-1-phenylethane.

The hydrocarbon represented by the aforementioned general formula (2) is specifically (o-ethylphenyl)phenylmethane or 1-(o-ethylphenyl)-1-phenylethane.

The mono-olefin hydrocarbon or the di-olefin hydrocarbon represented by the aforementioned general formula (3) is specifically (m-vinylphenyl)phenylmethane (mono-olefin hydrocarbon) obtained by dehydrogenating an ethyl group which is substituted at the m-position of a phenyl group of (m-ethylphenyl)phenylmethane, 1- (m-vinylphenyl)-1-phenylethane (mono-olefin hydrocarbon) obtained by dehydrogenating an ethyl group which is substituted at the m-position of a phenyl group of 1-(m-ethylphenyl)phenylethane, 1-(m-ethylphenyl)-1-phenylethylene (mono-olefin hydrocarbon) obtained by dehydrogenating an ethyl group to which two phenyl groups of 1-(m-ethylphenyl)-1-phenylethane are substituted, and 1-(m-vinylphenyl)-1-phenylethylene (di-olefin hydrocarbon) obtained by dehydrogenating both an ethyl group which is substituted at the m-position of a phenyl group of 1-(m-ethylphenyl)-1-phenylethane and an ethyl group to which two phenyl groups are substituted.

The dehydrogenated compound of an o-ethyldiphenylalkane is merely prepared by a dehydrogenation reaction of the o-ethyldiphenylalkane represented by the general formula (2), and the dehydrogenated compounds of the o-ethyldiphenylalkane are mainly a cyclo-dehydrogenated compound shown as described below and a compound from which an ethyl group substituted at a phenyl group is eliminated.

Namely, the cyclo-dehydrogenated compound prepared from the o-ethyldiphenylalkane is as follow.

1-Phenylindene and the like are prepared from (o-ethylphenyl)phenylmethane. 1-Phenylnaphthalene (boiling point: 324–325° C.), 9,10-dimethylanthracene (melting point: 182–184° C.), and 9-methylanthracene obtained by elimination of a methyl group of 9,10-dimethylanthracene, anthracene (melting point: 216–218° C., boiling point: 342° C.) and the like are prepared from 1-(o-ethylphenyl)-1-phenylethane.

These cyclo-dehydrogenated compounds are liquids having a high boiling point in comparison with the dehydrogenated compound of the m-ethyldiphenylalkane or solids, and can be easily separated by distillation. 9,10-Dimethylanthracene, 9-methylanthracene and anthracene being solids at normal temperature can be easily separated by also depositing crystals by cooling and the like to be filtered.

Concerning the compound obtained by elimination of an ethyl group substituted at a phenyl group of the o-ethyldiphenylalkane, diphenylmethane (boiling point: 264.5° C.) is prepared from (o-ethylphenyl)phenylmethane, and diphenylmethane and 1,1-diphenylethylene (boiling point: 277.0° C.) and the like are prepared from 1-(o-ethylphenyl)-1-phenylethane. These are compounds having a low boiling point in comparison with the dehydrogenated compound of the m-ethyldiphenylalkane, and can be easily separated by usual distillation.

Therefore, the aforementioned cyclo-dehydrogenated compound prepared from the o-ethyldiphenylalkane and the aforementioned compound obtained by elimination of an ethyl group substituted at a phenyl group can be industrially and easily separated from the dehydrogenated compound prepared from the m-ethyldiphenylalkane which is the objective product of the present invention.

The ethyldiphenylalkane which is the starting raw material of dehydrogenation or oxidative-dehydrogenation reaction in the present invention is a mixture of the m-ethyldiphenylalkane and the o-ethyldiphenylalkane, and the proportion of the m-ethyldiphenylalkane or the o-ethyldiphenylalkane in the mixture is not specifically limited.

However, it is usually preferable to use a mixture raw material in which the content of the o-ethyldiphenylalkane (the total weight of the hydrocarbon represented by the general formula (2)) is in a range of 1–40% by weight (based on the total weight of the m-ethyldiphenylalkane represented by the general formula (1) and the o-ethyldiphenylalkane represented by the general formula (2)).

When the content is less than 1% by weight, it is difficult to reveal the effect of the present invention because the content of the o-ethyldiphenylalkane is too little. In addition, it is difficult to obtain a mixture having such low content of the o-ethyldiphenylalkane by an alkylation reaction, a disproportionation reaction, a condensation reaction and the like using alkyl benzene and the like as a raw material.

As a result, it is not preferable that such mixture becomes expensive. It is not preferable that as the mixture in which the content of the o-ethyldiphenylalkane exceeds 40% by weight has too much o-ethyldiphenylalkane, the burden caused by the successive purification operation becomes large.

(Ethylphenyl)phenylmethane or 1-(ethylphenyl)-1-phenylethane of the raw material may be those produced by any of processes such as a known alkylation reaction, a disproportionation reaction, a condensation reaction and the like. When it is produced by these processes, a mixture containing at least the m-ethyldiphenylalkane and the o-ethyldiphenylalkane is usually obtained.

Next, the process for producing the mixture containing the m-ethyldiphenylalkane and the o-ethyldiphenylalkane which is used in the present invention is illustrated according to the above-mentioned processes such as a known alkylation reaction, a disproportionation reaction, a condensation reaction and the like.

(Alkylation Reaction)

The process according to the alkylation reaction is a process in which an aromatic hydrocarbon reacts with an alkylating agent in the presence of an alkylating catalyst. As the aromatic hydrocarbon there are mentioned diphenylmethane, ethylbenzene, 1,1-diphenylethane and the like. As the alkylating agent there are mentioned halides such as ethyl chloride, benzyl chloride, and α-methylbenzyl chloride; alkenes such as ethylene; aromatic olefins such as styrene; alcohols such as ethyl alcohol, etc. The halides as the alkylating agent can be any one of fluoride, chloride, bromide and iodide.

In order to obtain (ethylphenyl)phenylmethane by an alkylation reaction, specifically, there may be a process of reacting diphenylmethane with, for example, ethyl chloride, ethylene, ethyl alcohol or the like as the alkylating agent in the presence of an alkylating catalyst, a process of reacting ethylbenzene with benzyl chloride, etc.

In order to obtain 1-(ethylphenyl)-1-phenylethane by analkylation reaction, there may be a process of reacting 1,1-diphenylethane with ethyl chloride, ethylene, ethyl alcohol or the like as the alkylating agent, a process of reacting ethylbenzene with styrene as the alkylating agent, a process of reacting ethylbenzene with α-methylbenzyl chloride as the alkylating agent, etc.

As the alkylating agent in the above-mentioned alkylation reaction there are mentioned acid catalysts such as a Lewis acid (Friedel-Crafts catalyst) such as $AlCl_3$, $AlBr_3$, $AlI_3$, $BF_3$, $FeCl_3$, $TiCl_4$, $ZrCl_4$, $ZnCl_2$ or the like, a protonic acid such as HF, $H_2SO_4$, HCl, $H_3PO_4$ or the like, etc. The alkylating agent may be also the above-mentioned catalyst alone or those combining 2 or more of catalysts.

In addition, an amorphous metal oxide such as silica-alumina and a solid acid such as crystalline aluminosilicate or the like such as zeolite become the alkylating agent.

For the amorphous metal oxide, there are mentioned silica-magnesia, silica-calcia in addition to silica-alumina, and further, there are mentioned silica-alumina treated with alkaline, silica-alumina supporting $W_2O_5$ and the like. For the zeolite catalyst, there are mentioned an A type zeolite, an X type zeolite, a Y type zeolite, mordenite, ZSM-5 and the like. In addition, there are may be also mentioned those ion-exchanged with cations of an alkali metal, an alkaline earth metal, and a transition metal such as a rare-earth metal or the like in addition to those in which the cation of zeolite is proton. Any of them can be used as the alkylating agent.

Further, a heteropolyacid is utilized in an alkylation reaction by an alkyl halide as an acid catalyst, and can be also used for producing the ethyldiphenylalkane. Examples of the heteropolyacid include 12-tungstophosphoric acid ($H_3PW_{12}O_{40}$), 12-tungstosilicic acid ($H_3SiW_{12}O_{40}$), 12-molybdophosphoric acid ($H_3PMo_{12}O_{40}$) and the like, and can be used as a homogeneous catalyst or a heterogeneous catalyst supported with a carrier such as silica or the like.

In case of reacting by a continuous flow type, the liquid hourly space velocity (LHSV) of the reaction raw material is selected from a range of 0.01–10.

Concerning the proportion of the aromatic hydrocarbon to the alkylating agent in the alkylation reaction, when the alkylating agent exists excessively against the aromatic hydrocarbon, a poly-alkylated aromatic hydrocarbon in which the aromatic ring of the aromatic hydrocarbon is substituted with many alkyl groups is apt to be produced. Accordingly, it is preferable to carry out the alkylation reaction under a condition in which the aromatic hydrocarbon exists excessively against the alkylating agent.

The reaction temperature can be made different according to the activity of alkylating catalyst and the like. It is preferable to react those having a highly alkylating activity at a lower temperature than room temperature in order to suppress the production of a poly-alkylated aromatic hydrocarbon and other by-products. In addition, when using a low activity alkylating agent, a process of reacting them by raising the temperature of the alkylation reaction near to the boiling point of the aromatic hydrocarbon of a raw material, and the like, can be adopted. The reaction temperature can be suitably selected according to the activity of the alkylation reaction. At all events, the temperature can be selected from a temperature range from a low temperature of room temperature or less near to the boiling point of the aromatic hydrocarbon of a raw material.

The alkylation reaction can be carried out using the aromatic hydrocarbon of a raw material as a solvent without another solvent, but other solvent can be used.

The solvent used includes $C_6H_5NO_2$, nitro alkanes such as $CH_3NO_2$, chloroalkanes such as $CH_2Cl_2$, $CH_3CN$, $CS_2$ and the like. When these solvents are utilized, a complex is formed with a catalyst such as a Lewis acid catalyst or the like, thereby the alkylating activity can also be suppressed. There are advantages that various side reactions can be suppressed thereby and the amount of a catalyst used can be reduced because the solubility of the catalyst is increased. In addition, an aliphatic hydrocarbon such as hexane, heptane or the like can be also used as the solvent.

(Disproportionation Reaction)

The process of obtaining (ethylphenyl)phenylmethane by the disproportionation reaction is a process of reacting diphenylmethane and ethylbenzene. The reaction is a reaction of transferring the ethyl group of ethylbenzene to the phenyl group of diphenylmethane (transalkylation). The process of producing 1-(ethylphenyl)-1-phenylethane by the disproportionation reaction is a process of reacting 1,1-diphenylethane and ethylbenzene. The reaction is a reaction of transalkylating the ethyl group of ethylbenzene to the phenyl group of diphenylmethane.

As the catalyst of the disproportionation reaction, acid catalysts such as a Friedel-Crafts catalyst, a solid acid catalyst and the like in like manner as the aforementioned alkylation reaction can be used. The reaction temperature can be selected from a temperature range from a low temperature of room temperature or less near to the boiling point of the aromatic hydrocarbon of a raw material. Further, for the raw material fed, diphenylmethane or 1,1-diphenylethane and ethylbenzene are fed at about equal mole. In case of reacting by a continuous flow type, the liquid hourly space velocity (LHSV) of the reaction raw material is selected from a range of 0.01–10.

(Condensation Reaction)

Production process by the condensation reaction is a process of condensing the aromatic hydrocarbons such as benzene, ethylbenzene and the like in the presence of an acid catalyst using a condensing agent. The condensing agent includes aldehydes such as formaldehyde, trioxane, paraformaldehyde, dimethoxymethane, acetaldehyde, paraldehyde, or their derivatives, halogenated hydrocarbons such as methylene chloride, dichloroethane, etc.

More specifically, the process for obtaining (ethylphenyl)phenylmethane by the condensation reaction is a process of condensing benzene with ethylbenzene in the presence of an acid catalyst using formaldehyde, trioxane, paraformaldehyde, dimethoxymethane, or methylenechloride or the like as a condensing agent. The process for obtaining 1-(ethylphenyl)-1-phenylethane by the condensation reaction is a process of condensing benzene with ethylbenzene using acetaldehyde, paraformaldehyde, or 1,1-dichloroethane or the like as a condensing agent.

As the catalyst of the condensation, acid catalysts such as a Friedel-Crafts catalyst, a solid acid catalyst and the like in like manner as the aforementioned alkylation reaction can be used. Mineral acids such as sulfuric acid, hydrochloric acid, phosphoric acid and the like, various type zeolites such as A type, X type, Y type, mordenite type, L type, T type, ZSM type and the like, cation-type ion-exchange resins such as amberist and the like, and acid catalysts such as a Friedel-Crafts catalyst such as $AlCl_3$, $AlBr_3$, $AlI_3$, $BF_3$, $FeCl_3$, $TiCl_4$, $ZrCl_4$, $ZnCl_2$ and the like, etc. can be preferably used.

The reaction temperature can be selected from a temperature range from a low temperature of room temperature or less near to the boiling point of the aromatic hydrocarbon of a raw material. Further, benzene, ethylbenzene and the condensing agent for the fed raw material are fed at about equal mole to be condensed. In case of reacting by a continuous flow type, the liquid hourly space velocity (LHSV) of the reaction raw material is selected from a range of 0.01–10. As the condensation reaction, water, an alcohol and the like are produced as by-product. Accordingly, processes such as reaction-distillation and the like can be adopted at the condensation reaction.

When reactions such as the alkylation reaction, the disproportionation reaction, the condensation reaction and the like are carried out using alkylbenzene and the like as the raw material as mentioned above, a mixture containing at least the m-ethyldiphenylalkane and the o-ethyldiphenylalkane which are the raw material of the present invention is usually obtained.

(Dehydrogenation Reaction)

In the present invention, the dehydrogenation reaction is carried out using the above-mentioned mixture containing at least the m-ethyldiphenylalkane and the o-ethyldiphenylalkane as the raw material. The process can be carried out by a known liquid phase reaction or a gas phase reaction, but the gas phase reaction is usually preferable.

For the dehydrogenating catalyst used in the present invention, a dehydrogenating catalyst at production of styrene from ethylbenzene can be used.

As the dehydrogenating catalyst, for example, a catalyst having iron oxide, chromium oxide or a mixture of these oxides as main components are mentioned. Specifically, there are mentioned a transition metal oxide such as $Cr_2O_3$—$Fe_2O_3$—$K_2O$ series, a solid acid such as silica-alumina, a Pd-KBr/$\alpha$-$Al_2O_3$ catalyst, a thermally decomposed product of a polyacrylonitrile, and the like.

As an auxiliary catalyst, oxides of molybdenum, vanadium, manganese, zinc, copper and the like may be contained. Further, in order to improve the dehydrogenation efficiency, a catalyst to which oxides of sodium, potassium, magnesium, calcium, barium and the like of alkali metals and alkaline earth metals are added may be used. Further, a supported catalyst supported on carriers such as alumina, silica, silica-alumina and the like, may be used.

As the dehydrogenation reaction is an equilibrium reaction and a reaction in which the number of mole increases, a low reaction pressure is advantageous. Further, as the dehydrogenation reaction is an intensive endothermic reaction, a high reaction temperature is advantageous.

Therefore, the reaction pressure is a reduced pressure to 0.5 MPa, and preferably a reduced pressure to about 0.3 MPa. The degree of reduced pressure can be suitably set from the tolerance of a reaction equipment against the reduced pressure, and the like. The reaction temperature is within a range of 500° C. to 700° C., and preferably a range of 550° C. to 650° C. When a temperature is less than 500° C., the dehydrogenation reaction hardly proceeds, and when it exceeds 700° C., it is not preferable to cause a side reaction such as decomposition or the like.

In case of reacting by a continuous flow type, the liquid hourly space velocity (LHSV) of the reaction raw material is selected from range of 0.01–10.

It is preferable to carry out the dehydrogenation reaction by diluting in the presence of an inert gas. The inert gas which does not inhibit the dehydrogenation reaction can be suitably selected. For example, as the inert gas there are mentioned an organic gas such as methane in addition to an inorganic gas such as nitrogen, hydrogen, helium, argon, steam or the like. Considering the practicability of treatment, steam is preferably used. Steam can be coexisted within a range of a volume % of 0.01 to 10% in the reaction system.

In the dehydrogenation reaction, there are a simple dehydrogenation reaction of dehydrogenating as a hydrogen molecule which was described hitherto and an oxidative-dehydrogenation reaction using molecular oxygen as a hydrogen acceptor.

In the oxidative-dehydrogenation reaction, as exothermic reaction heat between hydrogen and the hydrogen acceptor is generated, it does not require a high temperature of 500° C. to 700° C. in like manner as the simple dehydrogenation reaction and can lower the reaction temperature. In addition, as it does not require a lot of steam which is a diluting gas and thermal medium (or can reduce), there is an advantage of effectively utilizing the reaction heat. In addition, there are many advantages on a process that an equilibrium constant becomes big and high conversion rate can be obtained.

Accordingly, the oxidative-dehydrogenation reaction can be utilized also in the production of the dehydrogenated compound of the m-ethyldiphenylalkane of the present invention.

As the oxidative-dehydrogenation reaction, for example, the catalyst for dehydrogenation of preparing styrene from ethylbenzene can be used as it is, and accordingly, the catalyst aforementioned as a dehydrogenation catalyst can be used. As the specifically preferable oxidative-dehydrogenation catalyst, for example, a transition metal oxide such as $Cr_2O_3$—$Fe_2O_3$—$K_2O$ series, a solid acid such as silica-alumina, a Pd-KBr/$\alpha$-$Al_2O_3$ catalyst, a thermally decomposed product of apolyacrylonitrile, and the like are mentioned.

As molecular oxygen being the hydrogen acceptor, air or pure oxygen can be used as it is, and further, these can be used together with an inert gas. The reaction can be carried out in the presence of molecular oxygen in the reaction system within a volume % range of molecular oxygen of 0.01 to 10%. The reaction temperature is nearly the same as the case of the dehydrogenation reaction, and specifically in a range of 500° C. to 700° C. and preferably 500° C. to 600° C. Other reaction conditions can be the same as in the aforementioned dehydrogenation reaction. Although an oxygen-containing compound as an oxidation product is occasionally contained, the product is nearly similar as the product of the dehydrogenation reaction.

After the dehydrogenation reaction or the oxidative-dehydrogenation reaction, (m-vinylphenyl)phenylmethane [a product obtained by dehydrogenating an ethyl group which is substituted at a phenyl group of (m-ethylphenyl) phenylmethane], 1-(m-vinylphenyl)-1-phenylethane (a product obtained by dehydrogenating an ethyl group which is substituted at a phenyl group of 1-(m-ethylphenyl)-1-phenylethane), 1-(m-ethylphenyl)-1-phenylethylene (a product obtained by dehydrogenating an ethyl group which is substituted at two phenyl groups of 1-(m-ethylphenyl)-1-phenylethane), 1-(m-vinylphenyl)-1-phenylethylene (a product obtained by dehydrogenating both an ethyl group which is substituted at a phenyl group of 1- (m-ethylphenyl) -1-phenylethane and an ethyl group to which two phenyl groups are substituted) and the like, which are the hydrocarbon represented by the aforementioned general formula (3) of the objective product, are obtained by distilling the reaction mixture according to a suitable purification.

The above-mentioned distillation does not require a special distillation, and can be carried out by a usual distillation which is industrially operated. In addition, a known purification operation can be suitably carried out.

EXAMPLE 1

The present invention is further illustrated in detail according to Examples below, and the present invention is not limited to Examples unless the purport of the present invention is deviated.

REFERENCE EXAMPLE 1

Ethylbenzene and a HY type zeolite of a catalyst (ZC-50, manufactured by Shokubai-Kasei Kougyou Co., Ltd.) were charged in a reactor, and a mixture of ethylbenzene and styrene (molar ratio=1:1) was added dropwise over 2 hours while stirring at a reaction temperature of 130 to 140° C. After completion of the dropwise addition, the stirring was continued and the reaction was carried out at a reaction temperature of 130 to 140° C. for 3 hours. The total molar ratio of ethylbenzene to styrene was 4:1 and the HY type zeolite was used by 10% by weight of styrene. After completion of the reaction, the catalyst was precipitated and separated, and the supernatant liquid was filtered to obtain a reaction solution.

The greater part of the reaction solution was ethylbenzene. Ethylbenzene was removed by reduced distillation, and the product was analyzed by chromatography. The composition was 2.3% by weight of 1-(o-ethylphenyl)-1-phenylethane, 33.0% by weight of 1-(m-ethylphenyl)-1-phenylethane and 47.7% by weight of 1-(p-ethylphenyl)-1-phenylethane.

EXAMPLE 1

The rectification distillation of the reaction solution obtained in Reference Example 1 was carried out, and a fraction at a distillate temperature of 125 to 129° C. and a vacuum degree of 0.53 kPa (4 mmHg) was analyzed. As a result, 1-(o-ethylphenyl)-1-phenylethane was 7.1% by weight and 1-(m-ethylphenyl)-1-phenylethane was 92.3% by weight.

The dehydrogenation reaction was carried out by using the fraction as a raw material, and flowing the raw material (feeding speed of 5 ml/h) together with water (feeding speed of 200 ml/h) at a reaction temperature of 600° C. under atmospheric pressure through a continuous flow type reaction tube in which 20 ml of iron oxide type dehydrogenation catalyst (G-84C, manufactured by NISSAN GIRDLER CATALYST Co., Ltd.) having a particle size of 16 to 20 mesh in arrangement was filled. The liquid hourly space velocity [LHSV] of the reaction raw material at this time was 0.25. The reaction solution was cooled at the exit of the reaction tube, and gas and water were separated. Then, an oil layer of the reaction solution till 3 hours after starting the reaction was analyzed by gas chromatography.

The composition of the oil layer of the reaction solution is shown in Table 1.

EXAMPLE 2

A raw material having a composition of 3.6% by weight of 1-(o-ethylphenyl)-1-phenylethane and 96.4% by weight of 1-(m-ethylphenyl)-1-phenylethane which has a lower proportion of o-isomer in comparison with Example 1, was used as the raw material.

The dehydrogenation reaction was carried out by flowing the raw material (feeding speed of 20 ml/h) and water (feeding speed of 200 ml/h) at a reaction temperature of 600° C. under atmospheric pressure through a continuous flow type reaction tube in which 20 ml of the dehydrogenation catalyst was filled. The liquid hourly space velocity [LHSV] was 1.00 which was larger than that in Example 1. An oil layer of the reaction solution till 3 hours after starting the reaction was analyzed.

The composition of the oil layer of the reaction solution is shown in Table 1.

EXAMPLE 3

A raw material which is the same as in Example 1 was used.

The dehydrogenation reaction was carried out by flowing the raw material (feeding speed of 70 ml/h) and water (feeding speed of 675ml/h) at a reaction temperature of 600° C. under atmospheric pressure through a continuous flow type reaction tube in which 70 ml of the dehydrogenation catalyst was filled. The liquid hourly space velocity [LHSV] was 1.00. An oil layer of the reaction solution till 30 hours after starting the reaction was analyzed.

The composition of the oil layer of the reaction solution is shown in Table 1.

EXAMPLE 4

A raw material having a composition of 9.2% by weight of 1-(o-ethylphenyl)-1-phenylethane and 90.5% by weight of 1-(m-ethylphenyl)-1-phenylethane which has a higher proportion of o-isomer in comparison with Example 1, was used as the raw material.

The dehydrogenation reaction was carried out by flowing the raw material (feeding speed of 70 ml/h) and water (feeding speed of 675 ml/h) at a reaction temperature of 620° C. under atmospheric pressure through a continuous flow type reaction tube in which 70 ml of the dehydrogenation catalyst was filled. The liquid hourly space velocity [LHSV] was 1.00. An oil layer of the reaction solution till 48 hours after starting the reaction was analyzed.

The composition of the oil layer of the reaction solution is shown in Table 1.

TABLE 1

|  | Example 1 | Example 2 | Example 3 | Example 4 |
|---|---|---|---|---|
| Raw material composition: o-isomer (wt %)/m-isomer(wt %) | 7.1/92.3 | 3.6/96.4 | 7.1/92.3 | 9.2/90.5 |
| Liquid hourly space velocity of raw material [LHSV] (hr$^{-1}$) | 0.25 | 1.00 | 1.00 | 1.00 |
| Reaction temperature (° C.) | 600 | 600 | 600 | 620 |
| Product composition (wt %) | | | | |
| diphenylmethane | 1.5 | 0.8 | 1.2 | 2.0 |
| 1,1-diphenylethylene | 1.9 | 1.2 | 2.0 | 2.0 |
| 1-(o-ethylphenyl)-1-phenylethane | trace | trace | trace | trace |
| 1-(o-vinylphenyl)-1-phenylethane | trace | trace | 0.1 | 0.1 |
| 1-(o-ethylphenyl)-1-phenylethylene | 0.2 | trace | 0.2 | 0.3 |
| 1-(o-vinylphenyl)-1-phenylethylene | none | none | none | none |
| 1-(m-ethylphenyl)-1-phenylethane | 0.7 | 1.7 | 1.2 | 1.3 |
| 1-(m-vinylphenyl)-1-phenylethane | 10.9 | 26.2 | 24.8 | 16.6 |
| 1-(m-ethylphenyl)-1-phenylethylene | 0.8 | 1.7 | 1.3 | 1.4 |
| 1-(m-vinylphenyl)-1-phenylethylene | 62.4 | 60.7 | 57.7 | 66.0 |
| 1-phenylnaphthalene | 0.9 | 0.2 | 0.5 | 1.1 |
| anthracene | 0.5 | 0.1 | 0.6 | 0.7 |
| 9-methylanthracene | trace | trace | 0.2 | 0.4 |
| 9,10-dimethylanthracene | trace | trace | trace | 0.1 |

*Industrial Applicability

INDUSTRIAL APPLICABILITY

According to the process for producing hydrocarbons of the present invention, a mixture of an o-ethyldiphenylalkane and a m-ethyldiphenylalkane which are difficult to be separated by an industrial distillation, whose ingredients are difficult to be utilized as a mixture in the prior art, and which is easily obtained and further low cost, can be used as a raw material. When a dehydrogenating reaction is carried out using the raw material, the o-ethyldiphenylalkane in the mixture becomes a cyclo-dehydrogenated compound having a higher boiling point than the dehydrogenated compound of the m-ethyldiphenylalkane, a solid cyclo-dehydrogenated compound, and a compound obtained by eliminating an ethyl group which was substituted at a phenyl group, i.e., a compound having a lower boiling point than the dehydrogenated compound of the m-ethyldiphenylalkane. Accordingly, the dehydrogenated compound of the o-ethyldiphenylalkane can be easily separated from the dehydrogenated compound of the m-ethyldiphenylalkane by usually distilling a mixture of the dehydrogenation reaction after reaction. As a result, the dehydrogenating compound of the m-ethyldiphenylalkane which is the objective product of the present invention can be easily obtained in high purity.

The dehydrogenating compound of the m-ethyldiphenylalkane of the objective product of the present invention is useful as a synthetic raw material of α-(m-benzoylphenyl)propionic acid (tradename: Ketoprofen) of a profen analgesic.

What is claimed is:

1. A process for producing hydrocarbons, wherein a mono-olefin hydrocarbon and/or a di-olefin hydrocarbon represented by the following formula (3) is selectively produced comprising dehydrogenating or oxidative-dehydrogenating a reaction mixture of any one of hydrocarbons among the hydrocarbons represented by the following formula (1) and any one of hydrocarbons among the hydrocarbons represented by the following formula (2), and distilling said reaction mixture after said dehydrogenating or oxidative-dehydrogenating step:

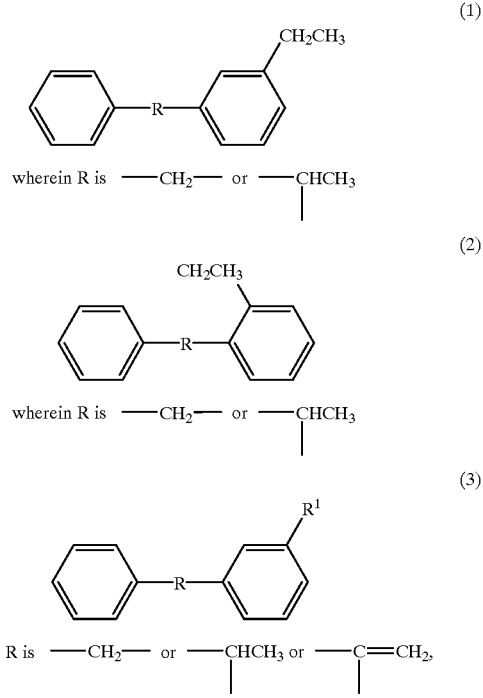

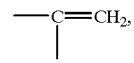

and/or $R^1$ is a vinyl group, and
further wherein said reaction mixture comprises, by weight, 1–40% of any one of the hydrocarbons represented by said formula (2) based on the total amount of hydrocarbons represented by formula (1) and formula (2).

2. A process for producing hydrocarbons according to claim 1 wherein said reaction mixture comprises the product of any of the alkylation of diphenylethane, diphenylmethane or ethylbenzene, the disproportionation of diphenylethane and ethylbenzene, or diphenylmethane and ethylbenzene and the condensation of benzene with ethylbenzene.

3. A process for producing hydrocarbons according to claim 1 wherein said reaction mixture comprises the product of the alkylation of diphenylethane, diphenylmethane or ethylbenzene.

4. A process for producing hydrocarbons according to claim 1 wherein said reaction mixture comprises the product of the disproportionation of diphenylethane and ethylbenzene, or diphenylmethane and ethylbenzene.

5. A process for producing hydrocarbons according to claim 1 wherein said reaction mixture comprises the product of the condensation of benzene with ethylbenzene.

6. A process for producing hydrocarbons according to claim 1 wherein the dehydrogenation produces a cyclo-dehydrogenated compound which is then separated from the reaction mixture by distillation and crystallization.

7. A process for producing hydrocarbons according to claim 1 wherein the dehydrogenation is carried out in a gas phase reaction.

* * * * *